United States Patent [19]

Schrock

[11] 4,164,217
[45] Aug. 14, 1979

[54] PREVENTIVE APRON

[76] Inventor: Rudy J. Schrock, Box 245, Rte. 2, Hartville, Mo. 65667

[21] Appl. No.: 851,851

[22] Filed: Nov. 16, 1977

[51] Int. Cl.² .............................................. A61B 19/00
[52] U.S. Cl. .................................................. 128/138 R
[58] Field of Search ............ 128/138 R, 138 A, 132 R

[56] References Cited

U.S. PATENT DOCUMENTS

| 1,720,439 | 7/1929 | Richardson | 128/132 R |
| 1,865,280 | 6/1932 | Risley | 128/138 R |
| 3,310,053 | 3/1967 | Greenwood | 128/132 R |

*Primary Examiner*—Lawrence W. Trapp
*Attorney, Agent, or Firm*—Rogers, Eilers & Howell

[57] ABSTRACT

A preventive apron used for control of human sexual conduct, especially the mentally retarded, has a main apron section which has on its inside a large pocket for receiving a rectangular box-shaped shield having an open side. The apron has upper, middle, and lower tie straps tied behind the user so that the main apron section is located in front of the body to place the shield in front of the genital area to prevent the wearer from contacting his or her genitals. The open side of the shield has a flange about its wall edges which acts to distribute force against the body of the user and to allow the shield to slide for comfort. The upper horizontal shield wall has a curved recess and flange which conforms to the shape of the lower abdomen of the user for a comfortable fit. The lower straps for the apron main section extend around each of the thighs and prevents the apron and shield from being pulled up. The shield is of such length and width that it covers the entire genital area and will not drop between the legs to contact the genital area when the legs are spread to the extent allowed by the apron.

11 Claims, 8 Drawing Figures

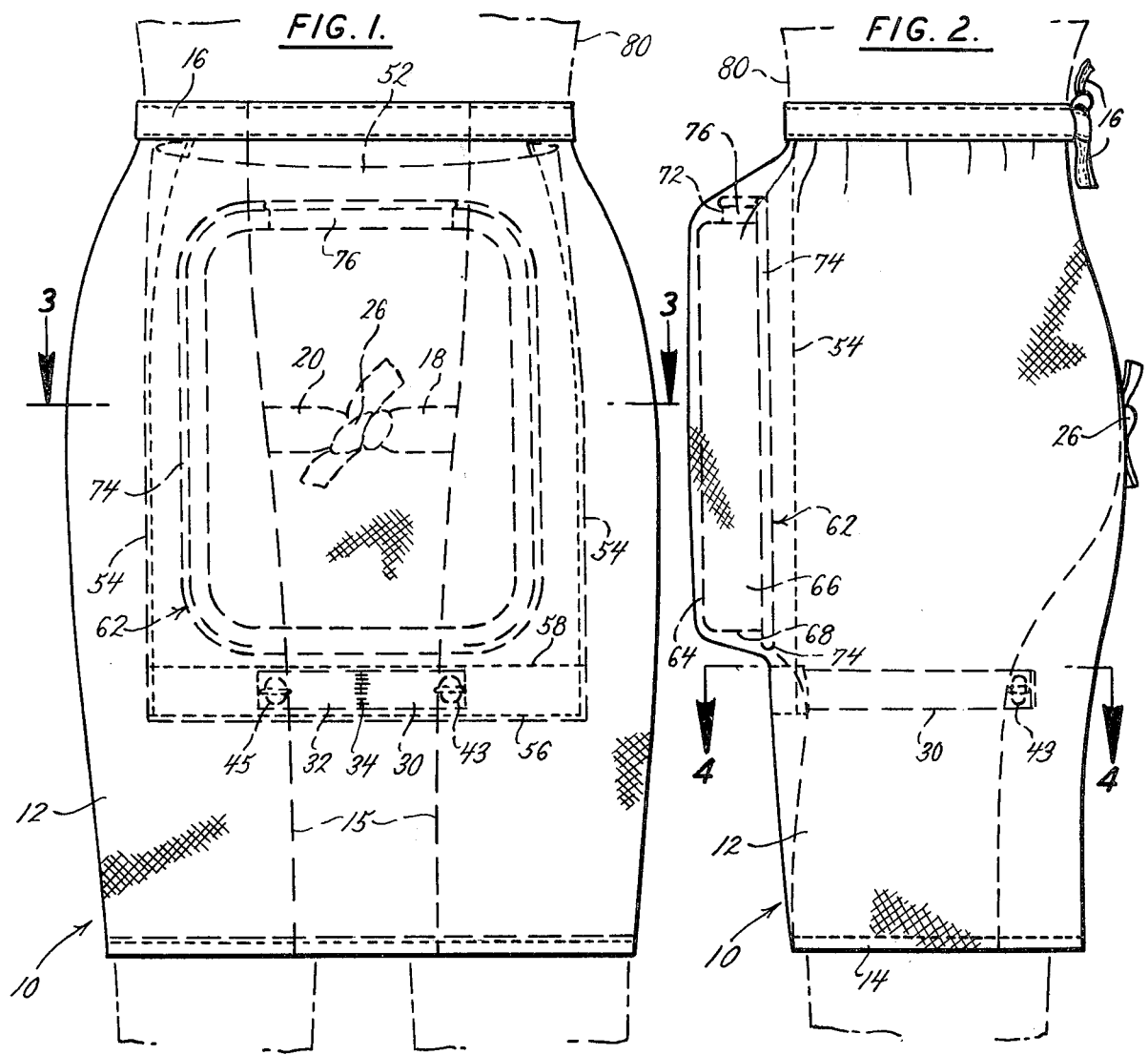

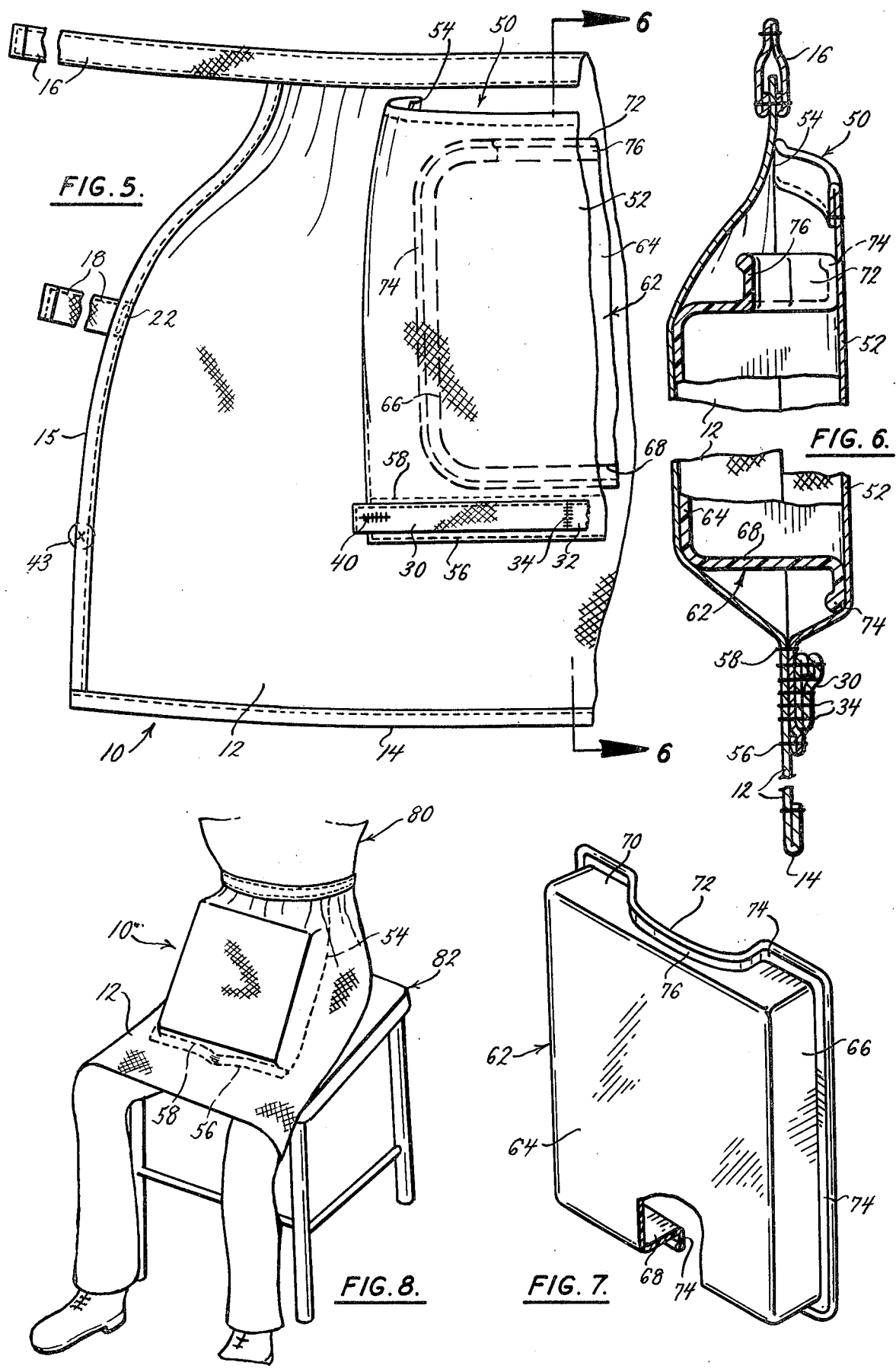

PREVENTIVE APRON

BACKGROUND, AND PRIOR ART, AND SUMMARY OF INVENTION

The field of the present invention concerns devices used to control sexual conduct of the mentally retarded, such as masturbation, and more particularly to those devices which are attached to the body for this purpose.

There are presently a large number of retarded people in the United States. The degree of mental retardation varies but there are a substantial number who have IQ's in the range of idiot, moron and imbecile. These mentally retarded people are in many cases unable to properly comprehend social settings in which they may be present, and it has been difficult in the past to control the sexual conduct of such retarded people in such social settings. This problem has been particularly acute among adolescents who have approached puberty. The retarded person, not being cognizant of proper behavior among others, in some instances will masturbate in the presence of a group, or in more severe instances make sexual advances upon another.

The presence of such conduct is undesirable, and of course is disruptive when it occurs in a group setting, and can be dangerous when an individual is attacked by a retarded person.

During the long period of time in which this problem has existed attempts have been made to restrain such sexual conduct. Pants without zippers have been tried. However these have proved to be uncomfortable, and the retarded person has been able to contact his or her genitals by virtue of rubbing the hand or some other object over the area of pants covering the genital area. Attempts have also been made to restrain the hands of the retarded person, but this is considered undesirable and still does not act as a total restraint. Corrective action such as scolding and the like have also not worked.

The present invention is designed to overcome problems of the prior art. The invention comprises a preventive apron which has a main apron section extending from the waist to the lower thigh region. The apron has a pair of top straps which wrap around the waist above the pelvis and are tied behind the back; a pair of midstraps which extend about and are tied behind the buttocks; and a pair of thigh straps which extend around each thigh and are secured to the interior of the apron. The apron further has a front interior pocket which receives a protective shield of rectangular box-shape. The shield has one side open and at its top end has a recess which conforms to the contours of the lower abdomen. The edge of the shield, rather than being the same width as the shield thickness, is extended into a flange that reduces the pressure exerted by contact of the shield against the body, and also allows some sliding of the shield for comfort.

The shield, which is preferably made of plastic, extends within the pocket from just above the lower abdomen area to beneath the midpoint of the thighs and is of sufficient width to prevent its falling between the legs of the user when the legs are spread to allow the wearer to rub the shield against the genital area. The box-shape of the shield allows its front side to be projected away from the genital area of the wearer so that the wearer is unable to rub the shield against the genital area.

When the apron is secured about the body with each of the straps secured tightly the wearer is unable to extend their hands downward into the apron to contact the genital area with the hand. The length of the apron restrains the wearer from extending the hand under the front of the apron into the genital area. The thigh straps prevent the apron from being pulled upward to lift the shield out of the way.

The tying and buttoning of the straps is sufficient in the case of a retarded person who is not intelligent enough to realize that the straps are fastened behind him or her can be untied to remove the apron. However, for a retarded child of somewhat higher intelligence, safety locks can be provided to secure the straps as mentioned so that the retarded person cannot loosen the apron straps.

The present invention thus provides a shield which restrains the user from masturbating in a group setting and further prevents sexual assault by virtue of the shielding action. The apron is shaped to allow the user to wear it and continue normal body movements, such as walking and bending, with minimal interference but provides the necessary shielding and thus overcomes the problems of the prior art.

DESCRIPTION OF THE DRAWINGS

FIG. 1 is a front view of the apron shown tied to the lower part of the body between the waist and the lower thighs, with the body being shown in dashed lines, and hidden portions of the apron being shown with hidden lines;

FIG. 2 is a view taken of the right side of FIG. 1 showing the apron tied to the body;

FIG. 3 is a section on the line 3—3 of FIG. 1 showing a midpoint of the apron, including the blocking shield;

FIG. 4 is a section taken on the line 4—4 of FIG. 2 showing the lower part of the apron and the lower straps tied about the thighs;

FIG. 5 is a rear view of the interior side of approximately a half of the apron shown in a spread position unfastened and away from the body;

FIG. 6 is a section taken on the line 6—6 of FIG. 5 showing the apron and illustrating the apron pocket which receives the blocking shield, with the midpart of the apron being broken in the drawing;

FIG. 7 is a perspective view of the blocking shield, with a lower part of the plate broken;

FIG. 8 is an illustration of the apron attached to the body of an individual sitting on a stool, with the legs spread outwardly.

DESCRIPTION OF THE PREFERRED EMBODIMENT

The preventive apron generally depicted as 10 in the drawings comprises a main cover section 12 which can be of durable cloth, such as denim and as seen in FIG. 5 extends from its upper end into a wider lower end. The cloth can have thickness of approximately 1/16 inch and can be, for example, denim. The main section 12 has its lower edge 14, and its side edges 15 hemmed and stitched. At the top of the main section 12 is a top strap 16 which can be of denim and is sewn securely to the upper end of the main section 12 and extends outwardly at both ends away from the main section 12 so that the ends can extend around the waist area of the user efficiently to allow the strap ends to be tied behind the users back when the apron is worn as seen in FIG. 2.

The main section 12 at its outer side edge 15 near the middle of section 12 has a pair of straps 18 and 20 each of which can be made of denim and which have their ends stitched to section 12 at 22, as seen for strap 18 in FIG. 5. The straps 18 and 20 are of sufficient length so that they can extend around behind the buttocks of the wearer and be tied in a knot 26 (FIGS. 2 and 3).

Beneath the mid straps 18 and 20 there are a pair of thigh straps 30 and 32 which can be denim, and have each inner end secured to the interior side of the middle of the apron by stitching at 34, as seen for strap 30, which stitching also passes through the lower edge of a pocket piece to be described. Each of the thigh straps 30 and 32 has a button hole at its outer end, such as the button hole 40 for strap 30 (FIG. 5). On the side edges 15 of the main section 12, beneath the mid straps 18 are a pair of buttons 43 and 45 each of which are secured by stitching to the outer edges 15. When the wearer has the apron on, the button holes of the thigh straps 30 and 32 are buttoned to the buttons 43 and 45 as seen in FIG. 4, to secure the apron main section around the thighs of the wearer.

In the middle of the inside of the apron main section 12 is a large pocket 50 which is used to receive and hold a preventive shield to be described. The pocket 50 comprises a layer of cloth, such as denim, 52 which has its side ends 54 stitched to the inside of the apron main section 12 from top to bottom of pocket piece 52. The bottom edge of pocket piece 52 is stitched across the midsection of the apron at 56 and 58 with the upper edge of the pocket piece 52 remaining free so that the pocket 50 is formed, being closed about each edge except the top edge.

As seen in the Figures the pocket 50 is large enough to adequately receive a blocking shield 62 which has a generally rectangular box-like shape with a flat front wall 64, two side walls 66, a bottom wall 68, and a top wall 70. The top wall 70 has a curved recess 72 designed to conform to the shape of the users lower abdomen for a comfortable fit. Around the entire part of the straight edges of the shield walls on the open side is an outwardly extending flange 74 which, by having an area wider than the width of the wall sections, allows for a spreading of any force exerted against the body of the wearer due to a force distributed against the shield 62. As seen in FIG. 7 the flange 74 extends into a curved flange section 76 about the recess area 72 to also fit the abdominal area. The shield 62 can be slid into the opening of the pocket so that the lower wall 68 wits into the lower end of the pocket as seen in FIG. 6. When the apron is detached from the body the shield can be slid in and out of the pocket 50 with ease.

OPERATION

The preventive apron 10 is used by attaching it to the body 80 of a human user by first inserting the shield 62 in the pocket 50 as previously described so that the shield is positioned as shown in the drawings with the front wall 64 of the shield towards the apron main section 12 and with the open end of the shield facing the pocket piece 52. The apron 10 is then held in front of the body with the pocket 50 towards the body and the ends of the strap 16 are extended about the waist of the user, preferably just above the pelvis, and tied together in a knot as seen in FIG. 16. The strap 16 should be tied snugly but should not be tied so as to bring discomfort to the user. After this, the mid straps 18 and 20 can be extended about the user's buttocks and tied together into knot 26 behind the buttocks so that the sides of the apron are snugly secured around the buttocks and the rear part of the thighs.

Then each of the thigh straps 30 and 32 are extended from section 12 towards the rear of the thigh and are secured to the rear interior side of the thigh by extending each of the buttons 43 and 45 through each of the end button holes at the ends of the lower straps. When the upper, middle, and thigh straps are thus secured, the main section 12 extends around the lower body portion between the waist line and just above the knees with the main section covering the front portion of this area and extending rearwardly behind the buttocks and thighs as seen in hidden lines in FIG. 1.

The shield 62 being housed within the pocket 50 is positioned in front of the genital area as seen in FIGS. 1, 2 and 8 to thus prevent the user from extending the hand over the genital area to masturbate. When the user sits down on a stool 82, as seen in FIG. 8, and the users legs are spread, the shield 62, because of its width will still be supported by the legs so that the shield does not drop downward into the genital area to allow it to be rubbed against the genitals. Because of the length of the shield, the user is also unable to extend the arms over the lower edge 14 of the main section 12 to contact the genital area. With the upper strap 16 having its ends snugly but firmly tied together the user is unable to extend the hand inside the apron top to contact the genital area.

The abdominal curved recess 72 and flange 76 of the shield fit comfortably against the lower abdomen of the user and therefore the pressure of the shield is distributed across the contours of the abdomen smoothly rather than all in the middle of the abdomen. The flange 74 which extends around the edge of the shield furthermore provides an area of contact against the body that is greater than the thickness of the walls 66, 68 and 70 to lessen the amount of pressure exerted by the shield by increasing the area of distribution of any force exerted upon the shield. The flanges 74 and 76 also allow for the shield to slide more easily against the body and eliminate binding which might result if the edges of the wall sections dug into the users body.

The presence of the walls 66, 68 and 70 also extends the front wall 64 outwardly from the genital area so that it cannot be rubbed against the genital area. The lower straps 30 and 32 which bind about the thighs beneath the crotch area prevent the apron and the shield from being pulled upwardly to expose the genital area.

The typical user of the apron is not intelligent enough to realize that the apron can be unfastened by untying the straps 16, 18 and 20 & 30 and 32, and therefore their positioning behind the backside prevents them from being untied by the user. By being on the backside also they are not in view of the user. The knot tied in straps 16, and straps 18 and 20 can be secure square knots or other secure knots known in the art. In the case of a user who is intelligent enough to realize that untying the back knots can remove the apron, a small key operated lock or other lock can be used with an insertable part so that the ends of straps 16, and the ends of straps 18 and 20 can be locked together. Such a lock can also be provided to lock the ends of thigh straps 30 and 32 to the side edges 15 of the apron at the location of the buttons 43 and 45.

The apron when thus secured permits the user to walk and bend or kneel with minimum discomfort and restrain in body movements. The shield being positioned in front of the genital area also prevents the user from consummating a sexual assault upon another.

The shield 62 has been described as being preferably made of a plastic that provides rigidity to keep the walls of the shield from being bent inward but has some resiliency which prevents cracking or breaking. Other materials such as various types of metals like aluminum or steel could be used, as could material such as porcelain. However the plastic shield construction is preferred.

A greater or fewer number of the straps can be provided. The present invention thus overcomes many problems existent in the prior art and contributes greatly to the art.

Various changes and modifications may be made within this invention as will be readily apparent to those skilled in the art. such changes and modifications are within the scope and teaching of this invention as defined by the claims appended hereto.

I claim:

1. A protective device for control of sexual conduct of a person comprising:
    (a) a flexible front main apron section of a length extending from above the persons genital area to beneath the persons genital area and extending in front of the persons genital area;
    (b) a shielding member associated with the main section, the shielding member extending from a position above the genital area to a position beneath the genital area;
    (c) means for securing the main section to wrap around the thighs of the users lower body between the waist and the middle of the thighs.

2. The structure of claim 1 wherein the apron main section and shield extend to the middle of the thighs.

3. The structure of claim 1 wherein the apron main section and the shield extend beneath the middle of the thighs.

4. The structure of claim 1 wherein the main section has a pocket, and wherein the shield is mounted within the pocket.

5. The structure of claim 1 wherein the shield is plastic.

6. The structure of claim 1 wherein the shield is shaped to project outwardly in front of the genital area.

7. The structure of claim 6 wherein the shield has an upper recess conforming to the shape of the lower abdomen of the user.

8. The structure of claim 6 wherein the shield has a flange extending about an edge facing the user for distribution of force exerted upon the shield to the body.

9. The structure of claim 6 wherein the shield is of rectangular box-shape.

10. The structure of claim 1 wherein the means to secure comprises a tie member secured to the main section and extending therefrom about a thigh of the user with means for securing the tie member to the main section so that the tie member and apron extend completely about the thigh.

11. The structure of claim 1 wherein the main section is of cloth.

* * * * *